US008845530B2

(12) United States Patent
Bruce et al.

(10) Patent No.: US 8,845,530 B2
(45) Date of Patent: Sep. 30, 2014

(54) RESPOSABLE BIOSENSOR ASSEMBLY AND METHOD OF SENSING

(75) Inventors: Robert Bruce, Beaverton, OR (US); Richard G. Sass, Portland, OR (US); W. Kenneth Ward, Portland, OR (US)

(73) Assignee: iSense Corporation, Wilsonville, OR (US)

( * ) Notice: Subject to any disclaimer, the term of this patent is extended or adjusted under 35 U.S.C. 154(b) by 1084 days.

(21) Appl. No.: 11/966,685

(22) Filed: Dec. 28, 2007

(65) Prior Publication Data

US 2008/0161656 A1    Jul. 3, 2008

Related U.S. Application Data

(60) Provisional application No. 60/883,121, filed on Jan. 2, 2007.

(51) Int. Cl.
*A61B 5/00* (2006.01)
*A61B 5/1486* (2006.01)
*A61B 5/145* (2006.01)

(52) U.S. Cl.
CPC ..... *A61B 5/14532* (2013.01); *A61B 2560/0285* (2013.01); *A61B 5/14865* (2013.01); *A61B 5/0031* (2013.01); *A61B 2560/045* (2013.01); *A61B 5/6849* (2013.01)
USPC ........... 600/300; 600/347; 600/365; 600/386; 204/403.1

(58) Field of Classification Search
USPC ......... 600/306–309, 319–320, 316, 323–329, 600/332, 333, 339–341, 345–347, 354, 357, 600/365, 372, 386–392, 406, 423, 427, 486, 600/538; 128/920–925
See application file for complete search history.

(56) References Cited

U.S. PATENT DOCUMENTS 3,596,940 A * 8/1971 Horwitt et al. ................ 403/360
6,275,717 B1 * 8/2001 Gross et al. ................... 600/345

(Continued)

FOREIGN PATENT DOCUMENTS

| JP | 2002513602 | 5/2002 |
| JP | 2002526137 | 8/2002 |

(Continued)

OTHER PUBLICATIONS

Shults, M.C. et al., "A telemetry-instrumentation system for monitoring multiple subcutaneously implanted glucose sensors", IEEE Transactions on Biomedical Engineering, vol. 41, No. 10, Oct. 1994.*

*Primary Examiner* — William Thomson
*Assistant Examiner* — Marie Archer
(74) *Attorney, Agent, or Firm* — Schwabe, Williamson & Wyatt, P.C.

(57) ABSTRACT

A device, system, and method for delivering a device such as a sensor or fluid transport structure or a fluid transport structure sensor combination into, for example, mammalian skin and receiving, analyzing, and displaying signals from the device such as a sensor are disclosed. A system in accordance with embodiments of the present invention includes a reusable sensor assembly including a transmitter, microcontroller, and housing plus a disposable sensor assembly including a housing having an opening for receiving both the distal end of a biosensor, a sensor insertion guidance structure, and a transmission apparatus for transmitting signals received from the sensor to a reusable sensor assembly for transmission to an external electronic monitoring unit.

34 Claims, 7 Drawing Sheets

(56) References Cited

U.S. PATENT DOCUMENTS

| | | | |
|---|---|---|---|
| 6,885,090 B2* | 4/2005 | Franzon et al. | 257/678 |
| 7,494,465 B2* | 2/2009 | Brister et al. | 600/309 |
| 7,706,853 B2* | 4/2010 | Hacker et al. | 600/344 |
| 2003/0083645 A1 | 5/2003 | Angel et al. | |
| 2004/0162521 A1 | 8/2004 | Bengtsson | |
| 2005/0121322 A1* | 6/2005 | Say et al. | 204/403.1 |
| 2006/0183984 A1* | 8/2006 | Dobbles et al. | 600/316 |
| 2006/0183985 A1 | 8/2006 | Brister et al. | |
| 2006/0235285 A1 | 10/2006 | Brister et al. | |
| 2007/0066873 A1* | 3/2007 | Kamath et al. | 600/300 |
| 2007/0173708 A9* | 7/2007 | Dobbles et al. | 600/316 |
| 2008/0097246 A1* | 4/2008 | Stafford | 600/584 |
| 2009/0105569 A1* | 4/2009 | Stafford | 600/365 |

FOREIGN PATENT DOCUMENTS

| | | |
|---|---|---|
| JP | 2005514088 | 5/2005 |
| JP | 2006218305 | 8/2006 |
| WO | 2005/023097 | 3/2005 |
| WO | 2005/074161 | 8/2005 |
| WO | 2006/017358 | 2/2006 |
| WO | 20061124759 | 11/2006 |

\* cited by examiner

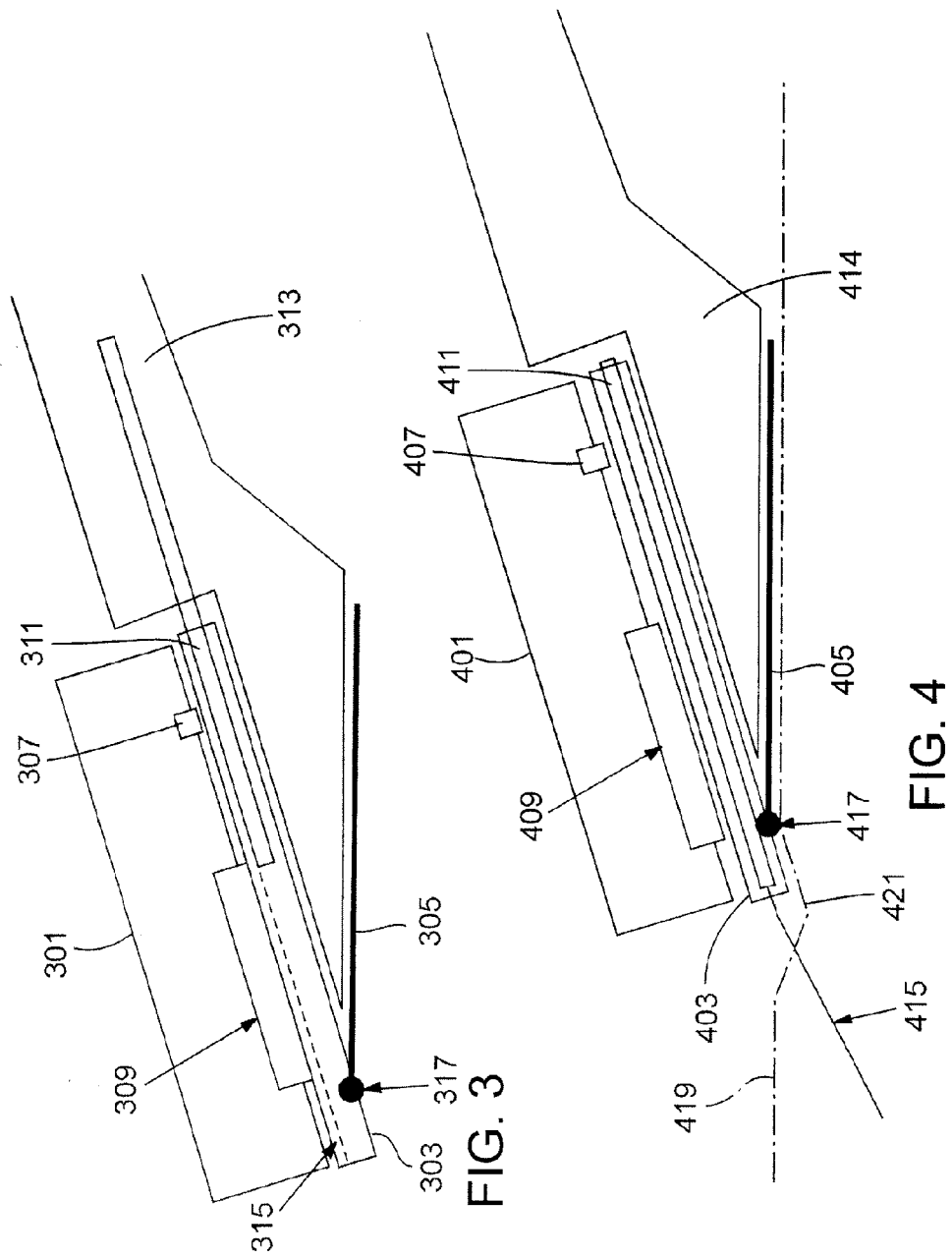

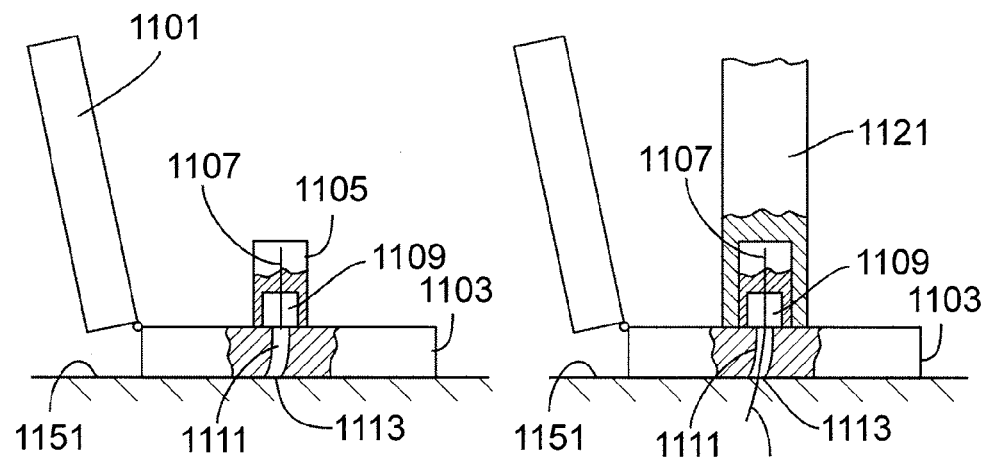
FIG. 11A
FIG. 11B
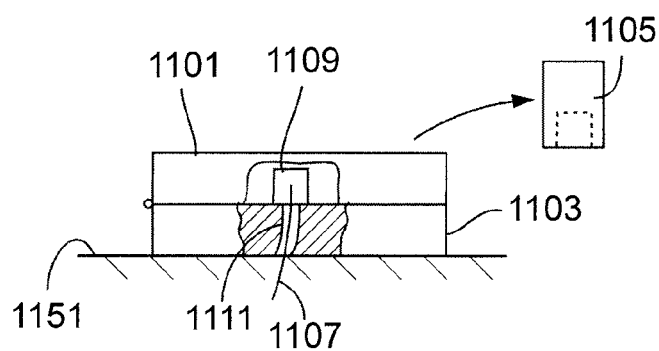
FIG. 11C

RESPOSABLE BIOSENSOR ASSEMBLY AND METHOD OF SENSING

CROSS REFERENCE TO RELATED APPLICATIONS

This application claims priority to U.S. Provisional Patent Application No. 60/883,121, filed Jan. 2, 2007. The entire disclosure of U.S. Provisional Patent Application No. 60/883,121, entitled "Resposable Biosensor Assembly and Method," is hereby incorporated by reference in its entirety.

TECHNICAL FIELD

This present invention relates generally to devices for delivering mechanically slender devices through skin into a body to perform various medical or physiological functions. More specifically, the present invention relates to an apparatus for transcutaneous placement of a soft cannula biosensor or flexible biosensor safely and automatically, using a resposable biosensor assembly having both a reusable and a disposable portion.

BACKGROUND

Many slender and flexible medical devices are designed to be inserted through the skin. For example, sensors facilitate the sensing of certain conditions within a patient. Electrochemical sensors are commonly used to monitor blood glucose levels in the management of diabetes. In one scheme, an electrochemical sensor incorporating an enzyme is fabricated onto a small diameter wire. A second reference electrode is also fabricated around the wire near the sensing electrode. The sensor assembly is inserted through the skin so that it is surrounded by interstitial fluid. A portion of the sensor remains outside the body, where electrical connections to the sensing electrode and reference electrode may be made. A suitable electronic measuring device outside the body may be used to measure electrical current from the sensor for recording and display of a glucose value, or other measurement. These types of devices are described, for example, in U.S. Pat. No. 5,965,380 to Heller et al. and U.S. Pat. No. 5,165,407 to Wilson et al.

In addition to electrochemical glucose sensors, a number of other electrochemical sensors measure the chemistry of blood or other body fluids or materials. Electrochemical sensors generally make use of one or more electrochemical processes and electrical signals to measure a parameter. Other sensors use optical techniques to perform a measurement.

Biosensors are sometimes housed in an apparatus that sits on the skin during operation. To prevent infection and for other reasons, the apparatus may be discarded after each use.

BRIEF DESCRIPTION OF THE DRAWINGS

Embodiments of the present invention will be readily understood by the following detailed description in conjunction with the accompanying drawings. To facilitate this description, like reference numerals designate like structural elements. Embodiments of the invention are illustrated by way of example and not by way of limitation in the figures of the accompanying drawings.

FIG. 3 shows a resposable sensor assembly and an insertion tool, in accordance with embodiments of the invention, prior to insertion of a biosensor;

FIG. 4 shows a resposable sensor assembly and an insertion tool, in accordance with embodiments of the invention, placed onto skin;

FIGS. 11A, 11B, and 11C show a resposable sensor assembly with a hinged RSA arrangement in accordance with embodiments of the present invention.

DETAILED DESCRIPTION OF THE EMBODIMENTS OF THE INVENTION

Figure 1:
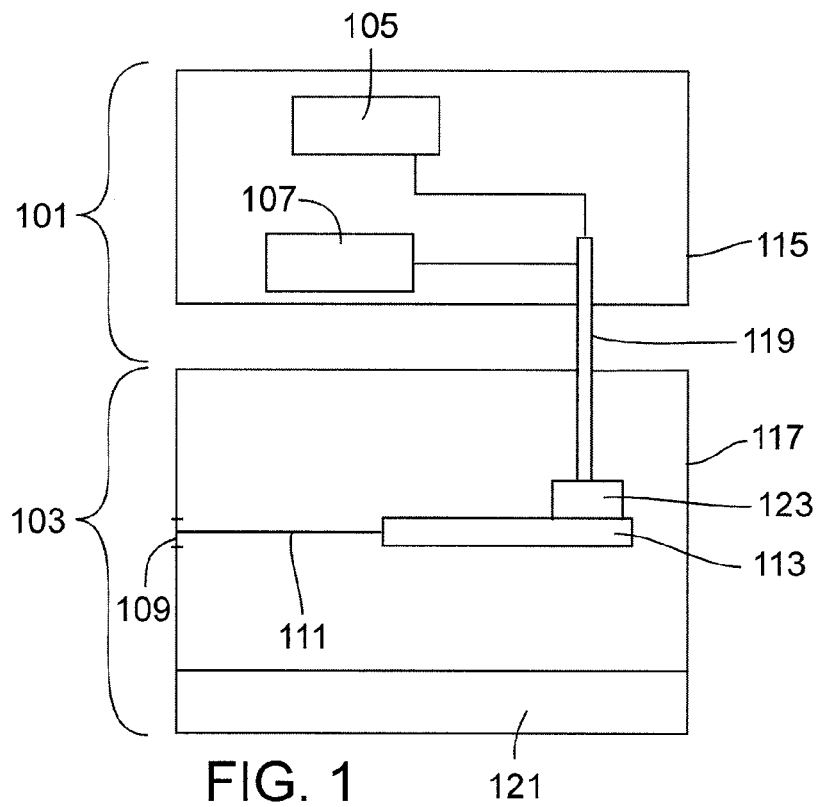
FIG. 1 shows a schematic representation of a resposable sensor assembly in accordance with embodiments of the present invention.

In the following detailed description, reference is made to the accompanying drawings which form a part hereof wherein like numerals designate like parts throughout, and in which is shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent. Also, not all operations are necessary; the inclusion of an operation in the description should not be construed to imply that it is necessary unless so stated.

The description (including the claims) may use perspective-based descriptions such as up/down, back/front, and top/bottom. Such descriptions are merely used to facilitate the discussion and are not intended to restrict the application of embodiments of the present invention.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with one another.

For the purposes of the present invention, a phrase in the form "A/B" or in the form "A and/or B" means "(A), (B), or (A and B)". For the purposes of the present invention, a phrase in the form "at least one of A, B, and C" means "(A), (B), (C), (A and B), (A and C), (B and C), or (A, B and C)". For the purposes of the present invention, a phrase in the form "(A)B" means "(B) or (AB)" that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

The term "actuator" refers to any of various electric, hydraulic, magnetic, pneumatic, or other means by which something is moved or controlled.

The phrase "sensor insertion guidance structure" means a physical structure that either guides an analyte sensor in a pre-determined direction, provides axial support to the sensor upon application of motive force to the sensor, or both. Additional details about suitable guidance structures may be found in U.S. patent application Ser. No. 11/558,394, filed Nov. 9, 2006, the entire contents of which are hereby incorporated by reference.

The term "axial support" means the support or bracing of a relatively straight, slender object when a motive force is applied to the object in such a way as to resist force vectors acting perpendicular to an imaginary line drawn through the device lengthwise; such support or bracing sufficient to prevent or reduce crimping, creasing, folding, or bending of the straight, slender object; or such support or bracing sufficient to enable the object to return to a relatively straight configuration after the motive force ceases to be applied such that the object substantially retains its original shape with minimal crimping, creasing, folding, or bending.

For the purposes of describing embodiments of the present invention and in the claims that follow, the term "electrical network" means electronic circuitry and components in any desired structural relationship adapted to, in part, receive an electrical signal from an associated sensor and, optionally, to transmit a further signal, for example to an external electronic monitoring unit that is responsive to the sensor signal. The circuitry and other components may or may not include a printed circuit board, a tethered or wired system, etc. Signal transmission may occur wirelessly with electromagnetic waves using, for example, RF communication, or data may be read using inductive coupling. In other embodiments, transmission may be over a wired or other direct connection.

Embodiments may provide a resposable sensor assembly comprising both a reusable sensor assembly (RSA) and a disposable sensor assembly (DSA). In an embodiment, an RSA may include, for example, a transmitter, a microcontroller, and a battery. In an embodiment, the microcontroller may be configured to receive measurement signals from an analyte sensor disposed within the DSA that has been partially inserted into animal skin; such as for example the skin of a human patient. The microcontroller may also be configured to cause the transmitter to transmit telemetry signals via RF or other mechanism in response to the received measurement signals. A separate monitoring device may monitor the received telemetry signals and provide useful information to a user, such as for example, a doctor, nurse, or patient regarding biological or physiological conditions measured by the analyte sensor. For example, a diabetic patient may wear the resposable sensor assembly to monitor their blood-glucose levels in real-time to better treat their condition.

In an embodiment, the battery of an RSA may be configured to power a transmitter and microcontroller. The battery may also be configured to power an analyte sensor of or associated with a DSA. In an embodiment, a DSA and RSA may be adapted to be removably secured to one another. That is, an RSA may be secured to a DSA in a way that facilitates communicative coupling between the microcontroller and analyte sensor, but may also be separated by a user after a period of time such as, for example, when the analyte sensor reaches the end of its useful life, or some other time period. At that point, the RSA may be attached to another DSA to form another resposable sensor assembly that may be attached either to the same or different patient. In this way, the relatively expensive components of the RSA—microcontroller, transmitter, battery—may be reused multiple times or indefinitely while the analyte sensor, which may have a much shorter useful life, may be discarded after each use. This may, in embodiments, make using the resposable sensor assembly to monitor biological or physiological conditions less expensive over the long-term than if the components of the RSA were discarded along with the DSA and the analyte sensor after each use. Further, enabling re-use of the RSA may result in a reduction of the amount of waste generated over time.

An embodiment of a resposable biosensor insertion apparatus (resposable sensor assembly) may include, as shown in FIG. 1, a reusable sensor assembly (RSA) 101 and a disposable sensor assembly (DSA) 103. The components of RSA 101, which may be encased in RSA housing 115, may include battery 107 and electrical network 105 electrically coupled to each other. The components of DSA 103, which may be encased within DSA housing 117, may include sensor 111 and support tube 113 each disposed at least partially within DSA housing 117. In embodiments, RSA housing 115 and DSA housing 117 may be made of, for example, molded plastic or other suitable materials. Guide tab 123 may be connected to support tube 113 and electrical connection 119. Electrical connection 119 may connect sensor 111 via intermediate electrical connections within guide tab 123 and support tube 113 to RSA 101. In embodiments, battery 107 may be a Lithium ion battery capable of running the device for a maximum time of between, for example, 3 days to 30 days, or more. In embodiments, battery 107 may be rechargeable and configured to be reused repeatedly. In embodiments battery 107 may be configured to be disposable. In embodiments, battery 107 may be configured to deliver power to DSA 103 in addition to powering electrical network 105 within RSA 101. In embodiments, battery 107 may be adapted to deliver anywhere from 50 mA-hr to 70 mA-hr, or more, thus enabling electrical network 105 to continuously transmit radio frequency (RF) or other electromagnetic signals to a separate monitoring unit for a period of approximately 3-7 days or more.

In embodiments, DSA 103 may be configured to be attached to skin using a variety of mechanisms including an adhesive substance or patch 121 secured to the bottom side of DSA 103. In embodiments in which patch 121 is utilized, patch 121 may be secured to DSA 103 using adhesive or a suitable mechanical means (clips, snaps, rails, etc.) and patch 121 may be configured to be further secured to skin using adhesive(s), bioresorbable staple(s), etc. In other embodiments, the resposable sensor assembly may be configured to be attached to a patient with a bandage.

In embodiments, patch 121 may be a breathable patch. In embodiments, some or all of a patch, the DSA, and/or RSA may include an antimicrobial agent/coating. In embodiments, patch 121 may have a site-centering hole patterned with an antimicrobial polymer coating patterned around an area directly adjacent to the biosensor insertion site. In embodiments, the coating may be, for example, silver ion, metallic silver, colloidal silver, silver salt, silver sulfadiazine or another form of silver. Silver is known to have antimicrobial characteristics. In embodiments, the coating may be silver combined with chlorine to form silver chloride. In embodiments, the coating may be silver/silver chloride. In embodiments, the antimicrobial coating may be in the form of a film that completely covers the site-centering hole and which may be pierced by sensor 111 upon insertion into skin.

In an embodiment, sensor 111 may be configured to be inserted through opening 109 and into animal skin by a suitable device (not shown) configured to supply a motive force to sensor 111. In embodiments, DSA 103 may contain a sensor insertion guidance structure configured to assist the passage of sensor 111 through opening 109 and to provide axial support to sensor 111 during insertion. In embodiments, sensor 111 may be configured to be inserted using, in part, support tube 113 into skin by any of various electric, hydraulic, magnetic, pneumatic, or manual actuator devices including, for example, linear solenoid actuators, rotary solenoid actuators, $CO_2$ cartridge actuators, spring actuators, air pump actuators, etc. In embodiments, actuators configured to deliver a high-speed motive force sufficient to drive a thin, flexible sensor into animal skin without the assistance of a sharpened introducer or similar device may be included. Additional details regarding such suitable actuators and sensor insertion guidance structures suitable for providing appropriate axial support may be found in U.S. patent application Ser. No. 11/558,394, filed Nov. 9, 2006, the entire contents of which are hereby incorporated by reference, and which describes a method and apparatus for insertion of an analyte sensor without the use of a sharpened introducer.

In embodiments, sensor 111 may be configured to be inserted using an actuator device not situated within DSA 103, such as for example, an actuator included within an inserter device that may be adapted to provide a sufficient motive force to an actuator when docked onto or placed next to DSA 103 or RSA 101 in a certain orientation and activated by a user or other activation mechanism.

In other embodiments, the resposable assembly may include a sharpened introducer configured to assist in the insertion of sensor 111 into skin. The introducer may be configured to be inserted by a patient manually or using the same or a different actuator device than that used to insert sensor 111. In embodiments, sensor 111 may be configured to be inserted simultaneously with or subsequent to the insertion of a sharpened introducer. Additional details about suitable sharpened introducers and associated insertion devices may be found in U.S. patent application Ser. No. 11/468,673 filed Aug. 30, 2006 the entire contents of which are hereby incorporated by reference, and which describes an apparatus and method for insertion of a sensor using a sharpened introducer inserted using human-provided motive force. Additional details may also be found in U.S. patent application Ser. No. 11/952,033 filed Dec. 6, 2007, the entire contents of which are hereby incorporated by reference and which describes the insertion of a sensor using a sharpened introducer which is inserted into skin using an actuator device either before or during sensor insertion.

In embodiments, DSA 103 and sensor 111 may be configured to be used for a maximum period of time of, for example, 5 to 15 days. In other embodiments, sensor 111 may be used for periods of time less than 5 days, or more than 15 days. When sensor 111 is no longer usable, DSA 103 may be configured to be discarded. In embodiments, RSA 101 may be configured to be detached from DSA 103 and reused with another DSA or similar device.

In embodiments, DSA 103 and RSA 101 may be configured to be connected prior to attachment of the combined device to skin. In embodiments, connection prior to skin attachment may allow easier connection if the device is to be attached to a patient's skin in an area of their body that is difficult to see such as, for example, on the lower portion of a patient's body if the patient has a large apron of abdominal fat. In other embodiments, DSA 103 and RSA 101 may be configured to be connected after attachment of RSA 101 or DSA 103 to the patient skin. In embodiments, sensor 111 may be configured to be inserted prior to attachment of RSA 101 to DSA 103.

In embodiments, both RSA 101 and DSA 103 may be configured to be directly secured to battery 107. Securing to battery 107 may, in embodiments, serve as the physical connection between RSA 101 and DSA 103. In other embodiments, RSA 101 and DSA 103 may be configured to be attached together using plastic catches, slides, rails, adhesives, or other mechanisms. In embodiments, circular catches on RSA 101 and/or DSA 103 may be configured to allow battery 107 to snap into RSA 101 and/or DSA 103.

In embodiments, electrical connection 119 may be a flex cable configured to provide a high-reliability, water-resistant interconnect to sensor 111 without requiring movable contacts on sensor 111 to maintain contact with sensor 111. In embodiments, electrical connection 119 may include slack and thus be configured to allow it to remain connected to guide tab 123 both during and after movement of both sensor 111 and guide tab 123 during the insertion process. Thus, in embodiments, sensor 111 may be configured to be connected to RSA 101 after attachment of RSA 101 to DSA 103 but before insertion of sensor 111. Thus, sensor 111 may be configured to be polarized prior to sensor insertion.

In embodiments, DSA 103 and RSA 101 may be configured to transfer signals using inductive coupling, allowing signals to pass without a direct electrical interconnect (such as electrical connection 119). In such embodiments, DSA 103 may be configured to generate magnetic affects or field changes using electrical signals from sensor 111 which may bridge an insulated gap between RSA 101 and DSA 103. RSA 101 may be configured to generate electrical signals using the magnetic affects or field changes and to propagate them within the circuitry of RSA 101. Electrical network 105 may be configured to receive such signals. In embodiments, DSA 103 may be configured to receive power from RSA 101 via inductive coupling.

In embodiments, electrical connection 119 may include intermediate circuitry (not shown) configured to assist in carrying signals from sensor 111 to electrical network 105.

In embodiments, electrical network 105 may include a transmitter configured to transmit signals to an electronic monitoring unit (not shown). Such signals may be conditioned or unconditioned measurement signals originating from sensor 111 and/or DSA 103. Such monitoring units may be configured to perform various calculations, analysis, and display of data. In addition, an electronic monitoring unit may be configured to provide an indication of an action to be taken based on the received data using various recommendation buttons or lights. Additional details about such display features may be found in U.S. patent application Ser. No. 11/558, 399 filed Nov. 9, 2006, the entire contents of which are hereby incorporated by reference and which describes the use of shape recognition methods, apparatuses, and systems to classify the shape of one or more recent glucose trends during continuous glucose monitoring and to warn the user when specific shapes or trends are identified. Sensor 111 may be configured to sense biological and/or physiological conditions, other than those related to blood glucose levels and trends. As such, display methods other than those taught by U.S. patent application Ser. No. 11/558,399 may also be utilized. Thus, U.S. application Ser. No. 11/558,399 is exemplary of data and display methods that may be practiced in accordance with the present invention.

In embodiments, electrical network 105 may be configured to receive an electrical signal from sensor 111 and to transmit a further signal to an external electronic monitoring unit or other device. In embodiments, electrical network 105 may comprise a variety of components in any desired structural relationship, whether or not the network has a printed circuit board, a signal conditioner, microcontrollers, analog to digital converters, wireless telemetry devices, transmitters, receivers, power controllers, antennas, etc. and whether or not it is a tethered or wired system, etc. In embodiments, such signal transmission may occur wirelessly with electromagnetic waves, such as RF communication. In embodiments, devices may be configured to read data using inductive coupling. In other embodiments, devices may be configured to transmit over a wire or other direct connection. In embodiments, electrical circuitry may be placed within RSA 101 so as to minimize or at least reduce the costs of DSA 103.

In embodiments, electrical network 105 may include a display along with digital logic configured to perform various calculations, analysis, and display of data received from sensor 111. In embodiments, circuitry may be provided that is configured to generate alarms viewable on a display or via light-emitting diodes, etc. In embodiments, such circuitry may be configured to generate an audible alarm. Exemplary alarms include: an out of range alarm in the event that the resposable biosensor insertion device is moved out of the range of transmission to an external electronic monitoring unit; threshold alarms in case the device detects signals from sensor 111 corresponding to dangerous or critical medical states; low battery conditions, etc.

In embodiments, a user may take the following steps to use the resposable biosensor insertion apparatus shown in FIG. 1. A user may remove DSA 103 from sterile packaging. The user may next place RSA 101 with battery 107 fully recharged onto the top portion of DSA 103. The user may then attach the resposable sensor assembly onto their skin. This may involve, in embodiments, the user removing a thin covering (for example a release liner) from the bottom of patch 121. The user may then insert sensor 111 using an integrated actuator device and/or separate insertion tool. Next, the user may be alerted by the resposable biosensor insertion apparatus or a separate electronic monitoring unit that sensor 111 needs to be calibrated. Calibration may be accomplished by the user with a finger stick blood test or other known method of calibration. A patient may then wear the device for a period of time such as, for example, 5 to 15 days or more. After the period for wearing the resposable sensor assembly has run, the user may remove the device from their skin, decouple RSA 101 from DSA 103, and dispose of DSA 103. The user may next place RSA 101 onto a new DSA 103 or other DSA removed from sterile packaging and repeat the process. In embodiments, battery 107 may be recharged when RSA 101 is decoupled from DSA 103 with battery 107 either separate from RSA 101 or integral with RSA 101 during recharging. Thus, in embodiments, the user may remove battery 107 from RSA 101 and recharge it separately. In embodiments, the recharging unit may include load test circuitry configured to test battery 107 and determine if it has enough remaining power to run the resposable sensor assembly for a specified length of time such as, for example, 1 to 15 days or more.

In various embodiments, the entire unit including the electronic circuit may be configured to be disposable. In an embodiment, a rechargeable battery may be configured to be reused from one on-skin application of the resposable sensor assembly to another. In embodiments, DSA 103 and/or RSA 101 may house a separate disposable battery. In embodiments, RSA 101 may not have a battery. In embodiments, RSA 101 may be configured to have power supplied by a battery in DSA 103 by a direct wired connection, inductive coupling, or other mechanism.

Figures 2A, 2B:
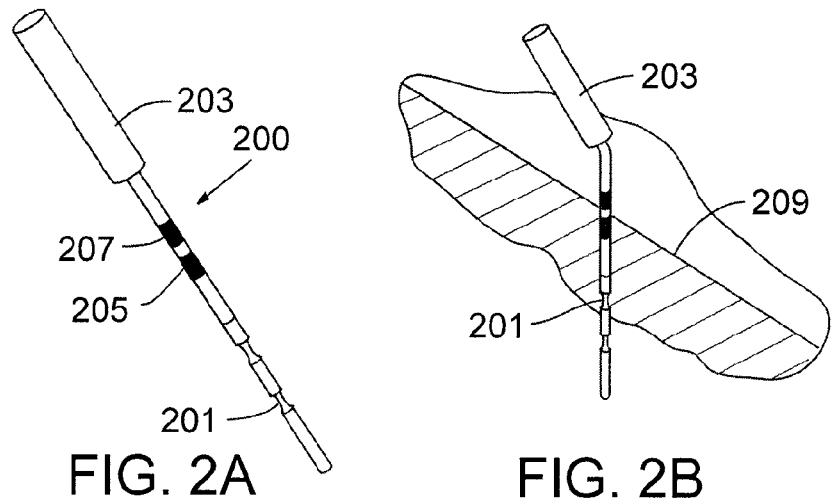
FIG. 2A illustrates an embodiment of an electrochemical glucose sensor that has been fabricated onto a length of thin, flexible wire in accordance with embodiments of the present invention.
FIG. 2B shows a cross-section of how an electrochemical sensor may appear when inserted into skin in accordance with an embodiment of the present invention.

FIG. 2A shows an analyte sensor 200 configured to be inserted into skin/tissue according to various embodiments of the present invention. In FIG. 2A, analyte sensor 200 may be an electrochemical glucose sensor fabricated onto a length of thin, flexible wire. A reference or ground electrode 205 and a sensing electrode 207 may be incorporated into analyte sensor 200. Small diameter end 201 (proximal end) of sensor 200 may be inserted through the skin. In an embodiment, this diameter may be approximately 0.25 mm or less. In an embodiment, the larger diameter end (distal end) of sensor 200 may include a sleeve of tubing 203, such as steel tubing or silver coiled wire, which may be configured to increase its rigidity and/or facilitate electrical connections. In some embodiments, the diameter of the larger section may be, for example, approximately 0.5 mm. In embodiments, the larger diameter portion of the sensor may be configured to remain outside of the body upon insertion. FIG. 2B shows a cross-section of sensor 200 inserted into skin 209. In embodiments, sensor 200 may be configured such that a portion of the length of sensor 200 may be implanted beneath skin 209, such as for example from 10-20 mm.

In embodiments, a sensor may be rigid or flexible. In some embodiments, a flexible sensor is one that may be flexed repeatedly, such as the type of flexion experienced by a subcutaneously implanted sensor in a human during normal movement, over a period of time (such as 3-7 days or more) without fracture. In embodiments, a flexible sensor may be configured to be flexed hundreds or thousands of times without fracture.

In embodiments, sensor 200 may have an enlarged portion at its distal end with an integrated power source, such as a battery, and an inner coil of electrically conductive wire disposed within the enlarged portion. An imagined axis of the inner coil of wire may run parallel to, or be collinear with, a segment of an imaginary line running through the length of sensor 200. A corresponding outer coil of electrically conductive wire, with a diameter larger than the inner coil, may be disposed within a DSA and/or RSA included as part of a resposable sensor assembly. The outer coil may be situated within the resposable device such that, when sensor 200 is inserted into skin, sensor 200 may sit within the circumference of the outer coil and an imagined axis of the outer coil may run parallel to, or be collinear with, the imagined axis of the inner coil. In such an arrangement, electrical signals generated from the sensor may propagate through the inner coil which may be configured to correspondingly generate a magnetic response in the outer coil which may, in turn, correspondingly generate electric signals in circuitry that the outer coil may be connected to. The resposable device may be configured to carry these corresponding signals to other electrical components of the resposable device. In this way, the sensor may be configured to communicate with the resposable device via inductive coupling without the need to include physical traces that directly connect sensor 200 to the resposable device.

FIG. 3 shows, in accordance with embodiments, a resposable sensor assembly with hinged support plate 305 and separate insertion tool 313. Reusable sensor assembly (RSA) 301 may be configured to be electrically coupled to disposable sensor assembly (DSA) 303 via electrical connector 307. In an embodiment, RSA 301 and DSA 303 may be configured to be physically connected. Battery 309 may be configured to power both an electrical network (not shown) within RSA 301 and sensor 315. In embodiments, a separate battery (not shown) may be configured to provide power to DSA 303 and be contained within DSA 303.

Support tube 311 may be attached to the distal end of sensor 315 and may, in an embodiment, extend out of the rear of DSA 303.

Support plate 305 may be configured to be attached to the bottom of DSA 303 via hinge 317. Support plate 305 is shown in an open position in FIG. 3 with an elongated angular end of insertion tool 313 placed between support plate 305 and DSA 303. Support plate 305 may be configured to be placed onto and attached to the skin of a patient. This attachment may be by an adhesive, bioresorbable staples, or other mechanism. An actuator (not shown) within insertion tool 313 may be configured to apply motive force to the distal end of support tube 311 which may, in turn, cause sensor 315 to pass through an opening in DSA 303 and be inserted into the skin of a patient. The angle of insertion tool 313 may provide a suitable angle for sensor 315 to enter the skin of the patient.

FIG. 4 shows a resposable sensor assembly placed onto skin 419 of a patient with sensor 415 inserted into skin 419 in accordance with embodiments. The resposable sensor assembly may be composed of reusable sensor assembly (RSA) 401 connected via electrical connection 407 to disposable sensor assembly (DSA) 403. The resposable assembly may be configured to be powered by battery 409. Sensor 415 may be configured to be supported at least in part by support tube 411. Hinged plate 405 may be attached to DSA 403 via hinge 417 and configured to be placed directly onto skin 419 and insertion tool 414 may be configured to be placed in between the bottom of DSA 403 and hinged plate 405.

The edge of DSA 403 may be configured to generate skin indentation 421 when the elongated angular end of insertion tool 414 is placed between DSA 403 and hinged plate 405. Skin indentation 421 may temporarily increase the natural tension in skin 419 to more easily allow skin 419 to be punctured with sensor 415. The opposite downward sloping surface of skin indentation 421 may also create an area of skin which presents an insertion angle less shallow with respect to the direction of the insertion path of sensor 415 than if skin indentation 421 were not present. This increased angle of insertion and skin tension may allow sensor 415 to puncture skin 419 upon insertion using less motive force and/or with less chance of deflection or bending of sensor 415. Additionally, the angling of the resposable sensor assembly during insertion may achieve a proper insertion angle without increasing the height of DSA 403.

Figure 5:
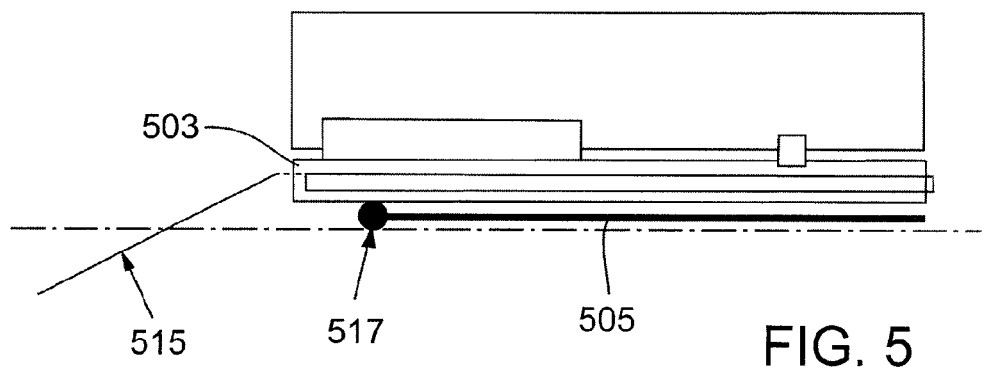
FIG. 5 shows a resposable sensor assembly in accordance with embodiments placed onto skin and with a biosensor inserted into skin.

FIG. 5 shows a resposable sensor assembly after insertion of sensor 515 and removal of an insertion tool in accordance with various embodiments of the present invention. After removal of an insertion tool, plate 505 may be configured to rotate about hinge 517 and may be, in embodiments, configured to come into contact with the bottom end of disposable sensor assembly (DSA) 503. Once the resposable sensor assembly is folded down, any prior local skin indention may disappear leaving sensor 515 inserted into the skin at an angle.

In embodiments, plate 505 may be secured to the bottom end of DSA 503 using any of various means including an adhesive, a catch, slide, rails, staples, or other mechanism. Securing may prevent unnecessary movement of the resposable sensor assembly and of sensor 515.

Figure 6:
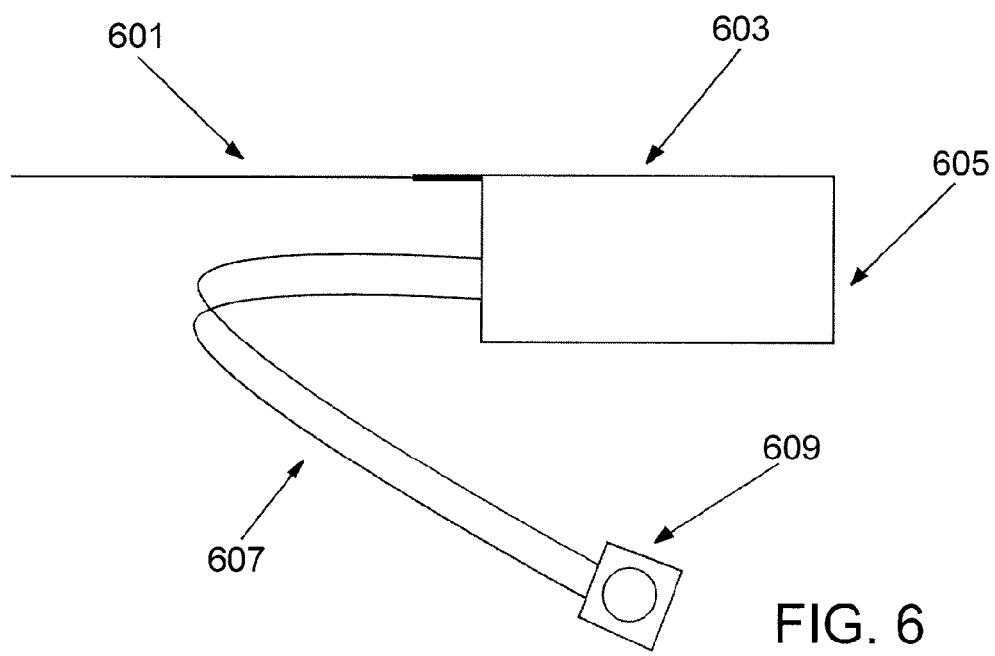
FIG. 6 shows a biosensor with a guide tab in accordance with embodiments of the invention.

FIG. 6 shows a sensor assembly in accordance with embodiments of the present invention. Sensor 601 is shown connected to support tube 603. Support tube 603 may be connected to guide tab 605 which may be connected to flex cable 607. Flex cable 607 may be configured to electrically couple guide tab 605 to watertight electrical connector 609. Guide tab 605 may contain electrical connections (not shown) configured to electrically couple it to sensor 601 via support tube 603. In embodiments, guide tab 605 may be electrically coupled directly to sensor 601. Electrical connector 609 may be attached to a reusable portion of a resposable sensor assembly at a fixed location which may facilitate water-sealing of the resposable sensor assembly. Slack in the configuration of flex cable 607 may allow movement of sensor 601 and guide tab 605 during the insertion process while maintaining the electrical connectivity of those components to a reusable sensor assembly (RSA). In embodiments, flex cable 607 may be constructed of an electrically conductive material such as, for example, copper or other conductive metal(s) surrounded by a dielectric material such as, for example, a flexible plastic material. The electrically conductive material may run the length of flex cable 607 in order to electrically couple guide tab 605 to electrical connector 609.

In embodiments, traces in flex cable 607 may be configured to extend the range of radio frequency transmission between an RSA and an electronic monitoring unit thereby allowing the resposable sensor assembly to operate a farther distance from the electronic monitoring unit.

Figure 7:
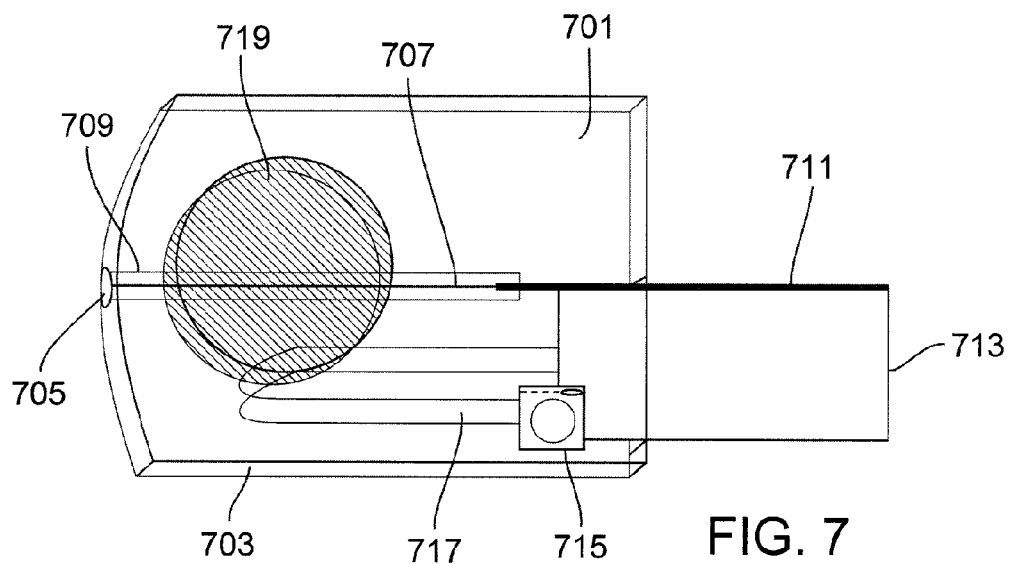
FIG. 7 shows a disposable sensor assembly portion of a resposable sensor assembly in accordance with embodiments of the invention.

FIG. 7 shows an open-top view of disposable sensor assembly (DSA) 701 in accordance with embodiments. DSA 701 may include DSA housing 703 with opening 705 connected to guidance structure 709. Sensor 707 may be situated inside guidance structure 709 prior to insertion. Support tube 711 and guide tab 713 may be connected to sensor 707 and electrically coupled to electrical connector 715 via flex cable 717. Electrical connector 715 may electrically couple a reusable sensor assembly (RSA) to DSA 701.

Additionally, housing 703 may include battery 719 which may be configured to supplement a battery included in a RSA. In embodiments, battery 719 may be configured to keep sensor 707 polarized prior to attachment of a RSA. In an embodiment, battery 719 may have a battery life matching or exceeding the maximum useable life of sensor 707 such as, for example, 1 to 15 days or more. In embodiments, battery 719 may be disposable. In other embodiments battery 719 may be rechargeable. In embodiments, DSA 701 may be attached to a RSA that includes no battery of its own. In alternative embodiments, DSA 701 may contain no battery.

Figure 8:
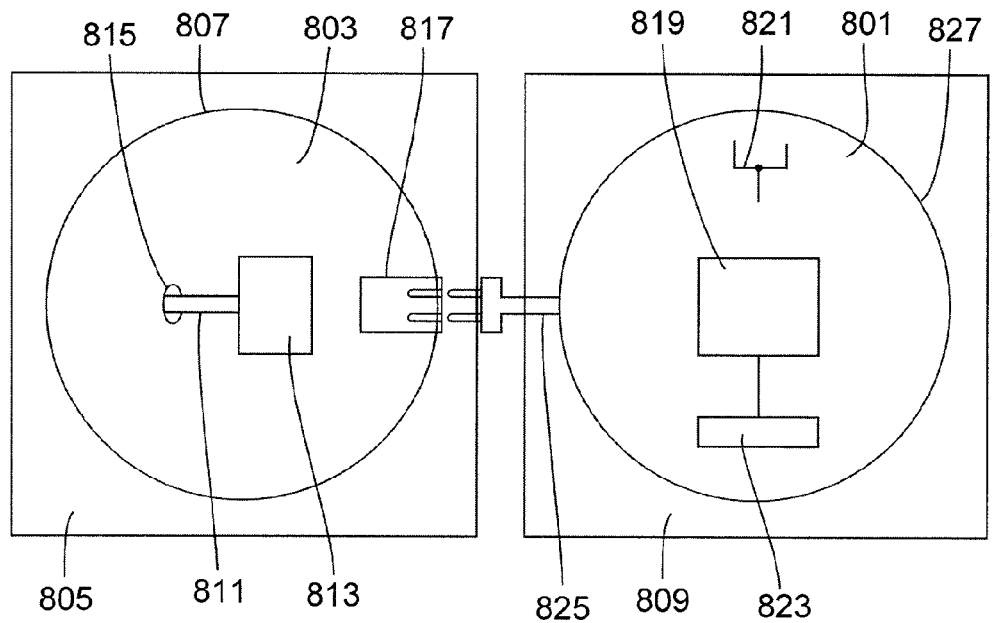
FIG. 8 shows a resposable sensor assembly with a reusable sensor assembly placed onto skin directly and a disposable sensor assembly also placed directly onto skin in accordance with embodiments.

FIG. 8 shows a resposable sensor assembly in accordance with embodiments of the present invention. Disposable sensor assembly (DSA) 803 may be placed on top of DSA patch 805 and reusable sensor assembly (RSA) 801 may be placed on top of RSA patch 809. RSA patch 809 and DSA patch 805 may be attached to the skin of a patient. In embodiments, RSA patch 809 and DSA patch 805 may be a variety of shapes, including square, rectangular, round, etc., and may be separate or connected in a variety of ways. While shown separated, RSA patch 809 and DSA patch 805 may be formed as a single patch with separate regions for RSA 801 and DSA 803. While patches are discussed above, in other embodiments, other securing mechanisms, such as adhesive, may be used instead of one or more patches.

In embodiments, RSA patch 809 and/or DSA patch 805 may be a breathable patch. In embodiments, RSA patch 809 and/or DSA patch 805 may have a site-centering hole patterned with an antimicrobial polymer with a coating dispersed around an area directly adjacent to the biosensor insertion site. In embodiments, the coating may be, for example, silver ion, metallic silver, colloidal silver, silver salt, silver sulfadiazine or another form of silver. Silver is known to have antimicrobial characteristics. In embodiments, the coating may include silver combined with chlorine to form silver chloride. In embodiments, the coating may include silver/silver chloride.

DSA 803 may include DSA casing 807 which may contain the various components of DSA 803. A sensor 811 may be configured to be positioned along with a guidance structure (not shown) next to insertion actuator 813. Insertion actuator 813 may be configured to apply a motive force to sensor 811 causing sensor 811 to pass through opening 815 situated on the bottom of DSA casing 807 and into the skin of a patient. In embodiments, DSA patch 805 may include a hole corresponding to opening 815 and thus configured to allow the passage of sensor 811 through opening 815, through the hole in DSA patch 805, and into the skin. In an embodiment, female electrical connector 817 may be included on DSA casing 807. DSA 803 may be situated on DSA patch 805 such that female connector 817 faces in the direction of RSA 801.

In embodiments, other electrical connecters may be used, such as for example a male connector. In embodiments, suitable electrical connectors may be configured and/or positioned to assist in the alignment of a DSA and RSA with each other and/or on an associated patch.

RSA 801 may be housed in RSA casing 827. Inside RSA casing 827 may be surface-mounted electronics 819. In embodiments, electronics 819 may be disposed on a printed circuit board. In embodiments, electronics 819 may be disposed on a flexible printed circuit board. In embodiments, electronics 819 may include microcontrollers, analog-to-digital converters, signal conditioners, power controllers, wireless telemetry devices, etc. In embodiments, some or all of those electrical components may be housed in DSA 803. Antenna 821 may be electrically coupled to electronics 819 and configured to facilitate radio frequency transmission to a separate electronic monitoring unit. In embodiments, a resposable sensor assembly may be configured to communicate with a separate electronic monitoring unit wirelessly with electromagnetic waves, such as RF communication, or may be configured to transmit data using inductive coupling. In other embodiments, a resposable sensor assembly may be configured to transmit over a wired or other direct connection.

In an embodiment, battery 823 may be integrated onto the top-side of RSA casing 827 for easy mounting onto a recharging unit, or for easy removal. In embodiments, battery 823 may be a Lithium ion flat pack battery. In other embodiments, other types of batteries may be utilized. Male connector 825 may be configured to be connected to female connector 817 to electrically couple RSA 801 to DSA 803. In embodiments, battery 823 may be configured to power the components of DSA 803 including sensor 811. In embodiments, electronics 819 may be configured to receive signals from sensor 811 sent as electrical signals to RSA 801 via female connector 817 and male connector 825. In embodiments, RSA 801 may be configured to receive signals from sensor 811 by inductive coupling or infrared signaling. In embodiments, DSA 803 may contain a battery (not shown) to maintain polarization on sensor 811 prior to attachment and to power sensor 811 after insertion.

In embodiments, male connector 825 may be, or may include, a flex cable. In embodiments, the traces inside the flex cable may be configured to extend the range of radio frequency transmission from RSA 801 to an electronic monitoring unit (not shown). This may, in embodiments, allow RSA 801, and therefore the patient onto whom it is attached, to move a greater distance from the electronic monitoring unit without disrupting transmission.

In embodiments, RSA 801 may be designed for reuse, for example, for up to 12 times in 3 months or 50 times in 1 year. In embodiments, RSA 801 may be configured to be used either more or less frequently. RSA 801 may be configured to be sterilized between uses using a medical autoclave, a sterilization system from Sterrad Systems, sterilization techniques using ethylene oxide gas, gamma radiation sterilization, etc. In embodiments, the resposable sensor assembly shown in FIG. 8 may be configured to be used on multiple patients with appropriate sterilization procedures.

In embodiments, RSA patch 809 may include rails (not shown) which may be configured to slidably engage with corresponding slides (not shown) on RSA 801 for ease of removal of RSA 801 without removal of patch 809 so that after the power of battery 823 runs out, a new RSA with a fully charged battery may be easily placed onto the patient and coupled to DSA 803 via male connector 825. In embodiments, DSA patch 805 and DSA 803 may include a similar rails and slides arrangement.

Figure 9:
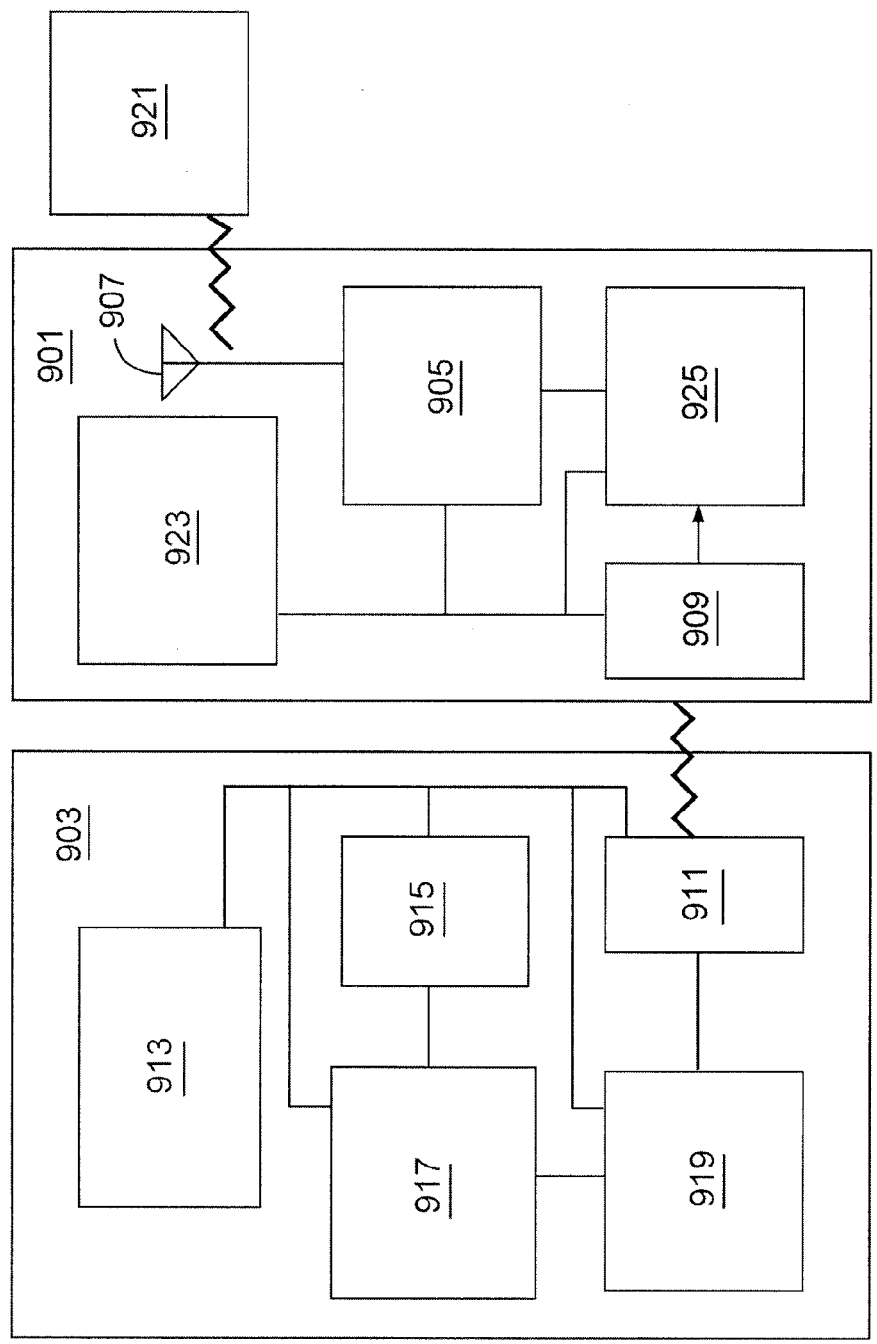
FIG. 9 shows a block diagram of the interaction of various electrical components and functions of a resposable sensor assembly in accordance with embodiments of the invention.

FIG. 9 shows a block diagram of electrical functions and components within a resposable sensor assembly in accordance with various embodiments. Reusable sensor assembly (RSA) 901 and disposable sensor assembly (DSA) 903 are shown in a side-by-side configuration. Other configurations are also possible such as, for example, stacked with RSA 901 situated above DSA 903 and vice versa.

RSA 901 may be configured to employ wireless telemetry 905 connected to antenna 907 for transmission of signals received from a sensor (not shown) to an automatic calibration and monitoring unit (ACMU) 921. In embodiments, wireless telemetry 905 may employ the Institute of Electronics and Electrical Engineers (IEEE) 802.15.4 low rate wireless personal area network (WPAN) standard. In other embodiments, wireless telemetry 905 may employ other IEEE 802.15 WPAN standards. In embodiments, wireless telemetry 905 may employ other wireless standards and/or protocols such as for example the Bluetooth or the ZigBee suite of protocols.

RSA 901 may also include RSA microcontroller 925 which may contain digital logic configured to, among other things, implement wireless telemetry 905. RSA microcontroller 925 may be configured to receive digital signals from receiver 909 (such as an infrared receiver) and may be configured to employ a selected wireless telemetry protocol and/or standard in order to prepare the received digital data for wireless transfer to automatic calibration and monitoring unit (ACMU) 921 in compliance with the selected wireless telemetry protocol.

DSA 903 may contain transmitter 911 (such as an infrared transmitter) configured to send signals received from a sensor to receiver 909. In embodiments, transmitter 911 may be configured to transmit using a wired connection, infrared transmission, inductive coupling, radio frequency (RF) transmission, etc. to transmit signals to receiver 909.

Sensor bias 915 may be coupled to sensor signal conditioning 917 and configured to provide a reference voltage to a sensor. Sensor bias 915 may be configured to polarize a sensor to condition it for use. Signal conditioning 917 may be configured to amplify, smooth out, transform, etc. a received sensor signal. In embodiments, DSA microcontroller 919 may be configured to implement an analog to digital conversion of the conditioned signal it receives. DSA microcontroller 919 may be configured to send the digitized signal to transmitter 911.

DSA 903 may also contain disposable power source 913 (such as a disposable battery). In embodiments, disposable power source 913 may be configured to maintain power to the sensor for as long as the sensor is intended to be inserted into the skin of a patient, or longer. In embodiments, disposable power source 913 may be configured to be discarded along with DSA 903 once its useful life has expired or once another prescribed period of time has elapsed. In other embodiments, disposable power source 913 may be a rechargeable battery that may be configured to be removed from DSA 903 and placed back into DSA 903, or into another DSA, after recharging.

RSA 901 may contain reusable battery 923. In embodiments, reusable battery 923 may be configured to maintain power to the sensor for as long as the sensor is intended to be inserted into the skin of a patient, or longer. In embodiments, reusable battery 923 may be configured to be discarded after a single use. In other embodiments, reusable battery 923 may be a rechargeable battery.

Embodiments may not include disposable power source 913. In such embodiments, reusable battery 923 may be configured to provide power to DSA 903 via a wired connection which may or may not be the same wired connection that connects receiver 909 to transmitter 911. In embodiments, DSA 903 may be configured to receive power via inductive coupling. Embodiments may not include reusable battery 923. In such embodiments, RSA 901 may be configured to receive power from disposable power source 913 via a wired connection or inductive coupling. Such a wired connection may or may not be the same wired connection that connects receiver 909 and transmitter 911. In embodiments where transmitter 911 and receiver 909 are configured to utilize infrared or other wireless technology, DSA 903 and RSA 901 may be configured to utilize a separate wired connection to provide/receive power to/from each other. In other wireless or infrared embodiments, DSA 903 and RSA 901 may be configured to utilize inductive coupling to provide/receive power. In embodiments, both disposable power source 913 and reusable battery 923 may be included.

Figure 10:
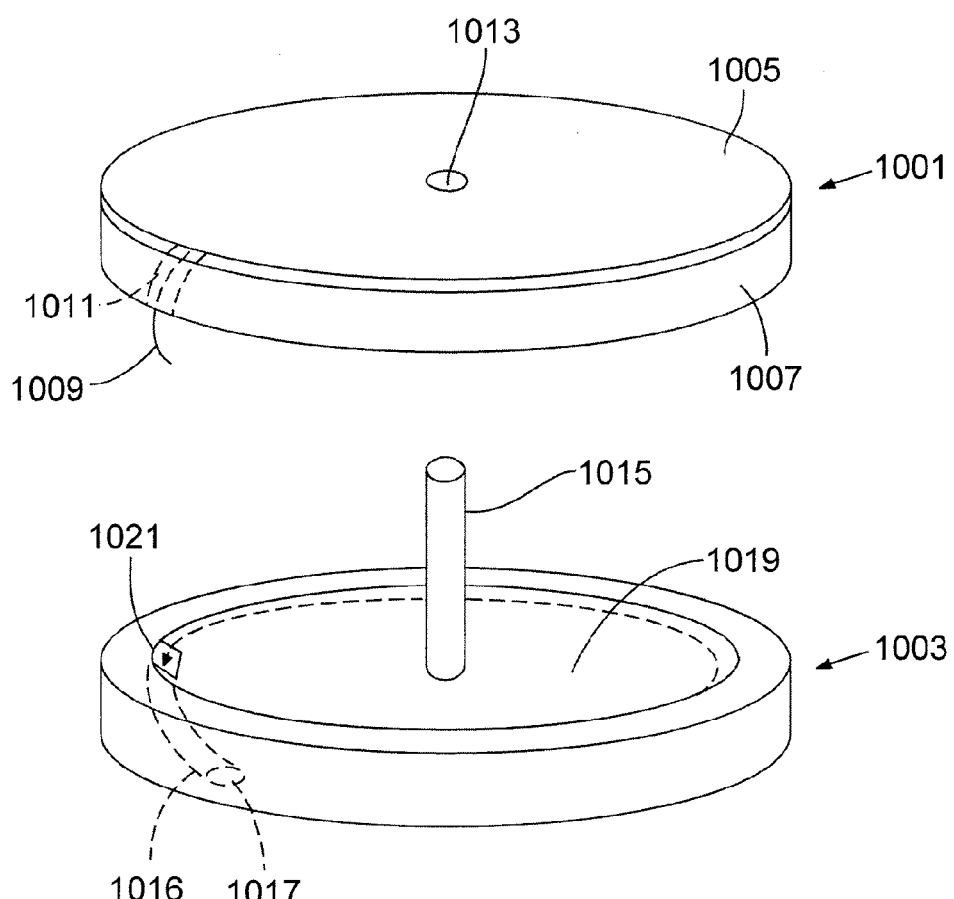
FIG. 10 shows a resposable sensor assembly with a mechanism for retracting an inserted biosensor into a disposable sensor assembly in accordance with embodiments of the present invention.

FIG. 10 shows a stackable resposable sensor assembly in accordance with various embodiments. Circular DSA 1001 may be configured to couple with indentation 1019 disposed within Reusable Sensor Assembly (RSA) 1003. Pass-through opening 1013 in DSA 1001 may be configured to correspond to shaft 1015 in the center of RSA 1003. DSA 1001 may be configured to be snapped into place using, for example, an interference fit. In embodiments, plastic rails (not shown) on the side of DSA 1001 may be configured to slide into corresponding grooves (not shown) on the edge of indentation 1019 and secure DSA 1001 and RSA 1003 using an interference fit. In embodiments, DSA 1001 may be configured to be secured into indentation 1019 using other mechanisms.

RSA 1003 may be configured to be placed onto skin prior to attachment of DSA 1001, or, in embodiments, DSA 1001 may be configured to be coupled to RSA 1003 prior to being placed onto skin. In embodiments, RSA 1003 may be configured to be attached to skin using an adhesive. In embodiments, a patch with adhesive substances on both sides may be used on the bottom of RSA 1003 and configured to attach RSA 1003 to skin. In an embodiment that utilizes a patch, a cut-out portion of the patch may be positioned to allow sensor 1009 to pass through the plane occupied by the patch so that sensor 1009 need not pass through the patch material when inserted.

In an embodiment, DSA 1001 may contain top plate 1005 and bottom plate 1007 which may each be configured to rotate relative to each other. Sensor 1009 may be configured to be placed inside DSA guidance structure 1011 within bottom plate 1007. Sensor 1009 may be attached at its distal end to top plate 1005 and be configured to be contained entirely within DSA guidance structure 1011. Pass-through opening 1013 may be shaped to correspond to a shape of shaft 1015 so that a particular orientation of DSA 1001 would be required to slide shaft 1015 into the top of RSA 1003. This may ensure that DSA guidance structure 1011 would line up with RSA guidance structure 1016 if DSA 1001 and RSA 1003 were so attached. RSA guidance structure 1016 may be curved and oriented through RSA 1003 to exit at bottom opening 1017. Top opening 1021 may sit within indentation 1019. When DSA 1001 is coupled properly with indentation 1019, DSA guidance structure 1011 may be configured to align with RSA guidance structure 1016 to form one continuous guidance structure through which sensor 1009 may be configured to pass during insertion.

In embodiments, an actuator (not shown) may be configured to be activated upon coupling of DSA 1001 with indentation 1019 and applying a motive force to sensor 1009 causing it to move through the combined guidance structure for insertion into skin through bottom opening 1017. In embodiments, a trigger mechanism may be configured to be pulled or pushed by the patient or another person after coupling of DSA 1001 to RSA 1003 in order to activate an actuator for sensor 1009 insertion.

In embodiments, sensor 1009 may be configured to be retracted from the patient's skin by a rotation of top plate 1005 relative to bottom plate 1007 and to subsequently exit the skin, pass through RSA guidance structure 1016, and wind completely into DSA 1001. DSA 1001 may be configured to be subsequently decoupled from indentation 1019 with sensor 1009 completely retracted and out of view aiding the psychological comfort of the patient.

In embodiments, electrical circuitry, including a microcontroller, an antenna, batteries, transmitter, signal conditioner, electrical coupler, infrared transmitter, receivers, etc. may be contained within DSA 1001, RSA 1003, or both. In embodiments, another device with electrical circuitry may be attached to the top of DSA 1001.

FIGS. 11A, 11B, and 11C show cross-sectional views of a resposable sensor assembly with a pivoting RSA arrangement in accordance with embodiments of the present invention. In FIG. 11A, RSA 1101 is shown pivoted upward relative to DSA 1103 situated on and/or adhered to skin 1151. DSA may be shaped, in embodiments, as a flat plate with an adhesive patch on the bottom side. Sensor cartridge 1105 may be a removable component of DSA 1103 and may include sensor 1107 prior to insertion. Sensor cartridge 1105 may be configured to fit over DSA docking socket 1109. It may be configured to hold sensor 1107 prior to insertion and to maintain it in a sterile condition. It may also include all or part of guidance structure 1111 to provide guidance and/or axial support to sensor 1107 during insertion. DSA docking socket 1109 may be configured to provide placement and/or orientation for sensor cartridge 1105 prior to insertion of sensor 1107. RSA 1101 may be configured to tilt using a hinged mechanism or other mechanism such as at a flexible point of the material comprising RSA 1101 or at a junction between RSA 1101 and DS 1103.

Guidance structure 1111 may extend from the bottom of DSA 1103 to the top portion of docking socket 1109. Guidance structure 1111 may be configured to provide axial support to sensor 1107 during insertion. In embodiments, guidance structure 1111 may be angled so as to allow sensor 1107 to be inserted into skin 1151 at an angle suitable for insertion. Pass-through opening 1113 may be situated on the bottom of DSA 1103 and at the terminal end of guidance structure 1111 so as to allow sensor 1107 to pass through the bottom of DSA 1103 during insertion. Guidance structure 1111 may be tube-shaped, or may have another geometry according to embodiments. In embodiments, guidance structure 1111 may be flat and may be configured to accommodate a molded part at the proximal end. Docking socket 1109 may be configured to also provide guidance and/or axial support to sensor 1107 during insertion.

FIG. 11B shows a cross-sectional view of a resposable sensor assembly coupled with inserter 1121 situated over sensor cartridge 1107 in accordance with embodiments. In embodiments, inserter 1121 may include an actuator (not shown) configured to be activated by a user and cause sensor 1107 to be inserted into skin 1151. Sensor 1107 is shown inserted into skin 1151. Inserter 1121 may be shaped in various ways to suit human factors and/or to accommodate the actuator. Inserter 1121 may be placed onto the top of DSA 1103 by a user. Docking socket 1109 may be configured to grip the proximal end of sensor 1107 after insertion and to provide a waterproof or water-resistant electrical connection between the resposable sensor assembly and sensor 1107 using a direct electrical connection, inductive coupling, or other mechanism.

FIG. 11C shows a cross-sectional view of a resposable sensor assembly with RSA 1101 tilted downward. After insertion, inserter 1121 may be removed by a user. When removed, inserter 1121 may be configured to extract sensor cartridge 1105 and drop it off for discard. In embodiments, RSA 1101 may be configured to be removably secured into place onto DSA 1103. RSA 1101 may include a removable or permanent outer cover. RSA 1101 may be configured to provide a waterproof or water-resistant electrical contact or an inductive coupling to sensor 1107 through docking socket 1109, when RSA 1101 is tilted downward and secured in place on top of DSA 1103.

As described elsewhere in this specification, RSA 1101 may be configured to receive electric measurement signals originating from sensor 1107 and transmit them to a separate monitoring unit. RSA 1101 may also contain reusable electronics, such as for example an RF or other transmitter, a microcontroller as described elsewhere in this specification, and a reusable/rechargeable battery. The embodiments shown in FIGS. 11A, 11B, and 11C may be used to limit the height and size of DSA 1103, by fitting a portion of DSA 1103 such as for example docking socket 1109 including a portion of guidance structure 1111 into a volume occupied by RSA 1101 when RSA 1101 is tilted downward onto DSA 1103. RSA 1101 may be of various sizes and shapes. In embodiments, RSA 1101 may fit over the entire top side of DSA 1103. Such an arrangement may balance the volume available for internal RSA 1101 components without increasing the footprint of DSA 1103.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A reusable sensor assembly (RSA) comprising:
 a RSA housing;
 a transmitter disposed within the RSA housing; and
 a microcontroller coupled to the transmitter, the microcontroller configured to be communicatively coupled to a disposable sensor assembly (DSA) having an analyte sensor, the microcontroller also configured to receive measurement signals from the DSA and to cause the transmitter to transmit telemetry signals in response to the received measurement signals;
 wherein, prior to insertion of the analyte sensor into skin, the analyte sensor is at least partially disposed within a DSA housing of the DSA and the analyte sensor is in contact with a sensor insertion guidance structure disposed in the DSA housing;
 wherein the RSA is removably secured to the DSA housing prior to and during the passing of the analyte sensor out the opening in the DSA housing; and
 wherein the sensor insertion guidance structure is configured to remain disposed in the DSA housing after insertion of the analyte sensor into skin and during receipt of the measurement signals by the RSA.

2. The RSA of claim 1 further comprising a battery disposed within the RSA housing and configured to supply electrical power to the disposable sensor assembly.

3. The RSA of claim 1 further comprising a RSA electrical connector disposed within the RSA housing and coupled to the microcontroller, and wherein the RSA housing is configured to be removably secured to a DSA housing of the DSA in an orientation that facilitates a communicative coupling of the microcontroller to the DSA via the RSA electrical connector.

4. The RSA of claim 3 wherein the RSA electrical connector is configured to communicatively couple the microcontroller to the DSA via a direct electrical connection with a DSA electrical connector of the DSA.

5. The RSA of claim 3 wherein the electrical connector is configured to facilitate a communicative coupling between the microcontroller and the analyte sensor prior to insertion of the analyte sensor and while the analyte sensor is in an inserted position.

6. The RSA of claim 1 wherein the RSA housing is configured to be removably secured to a DSA housing of the DSA in an orientation where at least a portion of a bottom surface of the RSA is flush against a top surface of the DSA housing, a bottom surface of the DSA housing adapted to be affixed to animal skin.

7. The RSA of claim 6 wherein the bottom surface of the RSA housing is configured to be tilted away from the top surface of the DSA housing while the RSA housing remains removably secured to the DSA housing.

8. The RSA of claim 1 wherein the RSA housing is adapted to be removably secured to the DSA housing to form a resposable sensor assembly, adapted to be removed from the DSA housing, and removably secured to another DSA housing to form another resposable sensor assembly.

9. The RSA of claim 1 wherein the microcontroller of the RSA is configured to be communicatively coupled with the DSA via inductive coupling.

10. The RSA of claim 1 wherein the RSA is configured to be coupled with the DSA prior to insertion of the analyte sensor and to remain coupled during insertion of the analyte sensor.

11. The RSA of claim 1 wherein the analyte sensor is disposed entirely within the DSA housing prior to insertion of the analyte sensor.

12. A disposable sensor assembly (DSA) comprising:
a DSA housing having an opening;
an analyte sensor disposed within the DSA housing prior to insertion of the analyte sensor into skin;
a sensor insertion guidance structure disposed within the housing and adapted to provide axial support to the analyte sensor and to allow the analyte sensor to at least partially pass through the sensor insertion guidance structure and out the opening upon application of motive force to the analyte sensor thereby placing the analyte sensor into an inserted position; and
a coupling device positioned on or in the sensor insertion guidance structure and adapted to facilitate a communicative coupling of the analyte sensor to a microcontroller of a reusable sensor assembly (RSA) while the analyte sensor is in the inserted position, the analyte sensor configured to generate measurement signals while partially inserted into animal skin and to transmit the measurement signals to the RSA via the communicative coupling;
wherein the analyte sensor is in contact with the sensor insertion guidance structure prior to insertion of the analyte sensor into skin;
wherein the RSA is removably secured to the DSA housing prior to and during the passing of the analyte sensor out the opening in the DSA housing; and
wherein the sensor insertion guidance structure is configured to remain disposed in the DSA housing after insertion of the analyte sensor into skin and during receipt of the measurement signals by the RSA.

13. The DSA of claim 12 wherein the coupling device on or in the sensor insertion guidance structure is adapted to facilitate the communicative coupling of the analyte sensor to the microcontroller while the DSA is removably secured to a RSA housing of the RSA.

14. The DSA of claim 13 wherein the coupling device is configured to facilitate the communicative coupling of the analyte sensor to the microcontroller prior to insertion of the analyte sensor and while the analyte sensor is in an inserted position.

15. The DSA of claim 13 wherein the coupling device is a DSA electrical connector adapted to be communicatively coupled to a RSA electrical connector disposed within the RSA housing.

16. The DSA of claim 15 wherein the DSA is adapted to receive electrical power from a battery of the RSA via the DSA electrical connector.

17. The DSA of claim 12 further comprising a transmitter configured to communicate with the microcontroller via a receiver of the RSA via infrared, direct electrical connection, a personal area network (PAN) transmission, or inductive coupling.

18. The DSA of claim 12 further comprising a docking socket disposed on a top surface of the DSA housing, wherein the sensor insertion guidance structure is disposed within the docking socket.

19. The DSA of claim 18 wherein the docking socket is configured to accept a removable sensor cartridge having the analyte sensor disposed within a cartridge guidance structure of the removable sensor cartridge, the sensor cartridge adapted to accept an inserter device containing an actuator configured to apply the motive force onto a distal end of the analyte sensor.

20. The DSA of claim 19 wherein the inserter is configured to extract the removable sensor cartridge from the docking socket after sensor insertion.

21. The DSA of claim 12 further comprising an adhesive patch disposed on an outside surface of the DSA housing and adapted to be adhered to animal skin.

22. The DSA of claim 12 wherein the DSA is configured to be coupled with the RSA prior to insertion of the analyte sensor and to remain coupled during insertion of the analyte sensor into skin.

23. The DSA of claim 12 wherein the analyte sensor is disposed entirely within the DSA housing prior to insertion into skin.

24. The DSA of claim 12 wherein the analyte sensor is at least partially extended from the DSA housing prior to insertion of the analyte sensor into skin.

25. A method comprising:
attaching, by a user, a resposable sensor assembly to skin of a patient, the resposable sensor assembly comprising a reusable sensor assembly (RSA) and a disposable sensor assembly (DSA), the DSA including an analyte sensor disposed at least partially within a DSA housing, the analyte sensor in contact with a sensor insertion guidance structure disposed in the DSA housing, and the RSA comprising a RSA housing, a transmitter disposed in or on the RSA housing, and a microcontroller disposed within the RSA housing, coupled to the transmitter, and configured to receive measurement signals from the analyte sensor, the microcontroller also configured to cause the transmitter to transmit telemetry signals in response to the received measurement signals; and
activating, by the user, an actuator to insert the analyte sensor partially into the skin;
wherein the RSA is removably secured to the DSA housing prior to and during the insertion of the analyte sensor into the skin; and
wherein the sensor insertion guidance structure is configured to remain disposed in the DSA housing after insertion of the analyte sensor into skin and during receipt of the measurement signals by the RSA.

26. The method of claim 25 wherein the RSA housing is adapted to be tilted upwards to expose a top surface of the DSA, the method further comprising:
fitting an inserter device onto a sensor cartridge covering a docking socket disposed on the top surface of the DSA, the inserter device containing the actuator, the sensor cartridge containing the analyte sensor;
removing the inserter device by the user upon activating the actuator, the removing of the inserter device causing an extraction of the sensor cartridge and an exposing of the docking socket; and
tilting, by the user, the RSA housing downward so that it covers the docking socket in a way that forms a communicative coupling between the docking socket and the microcontroller of the RSA.

27. The method of claim 25 wherein the RSA is coupled with the DSA prior to the activating and wherein the RSA remains coupled to the DSA during the activating.

28. The method of claim 25 further comprising, after a period of time, removing, by the user, the resposable sensor assembly from the skin surface including the analyte sensor, separating the RSA from the DSA, and attaching the RSA to another DSA to form another resposable sensor assembly.

29. The method of claim 28 further comprising attaching, by the user, the another resposable sensor assembly to either the skin surface, a different skin surface of the patient, or to a skin surface of another patient.

30. A resposable sensor assembly comprising:
a reusable sensor assembly (RSA) including:
a RSA housing; a transmitter disposed within the RSA housing;
a microcontroller coupled to the transmitter and configured to receive measurement signals from a disposable sensor assembly (DSA) and to cause the transmitter to transmit telemetry signals in response to the measurement signals; and
the DSA including:
a DSA housing having an opening;
an analyte sensor disposed within the DSA housing prior to being placed in an inserted position;
a sensor insertion guidance structure structurally integrated into the housing, and adapted to provide axial support to the analyte sensor and to allow the analyte sensor to at least partially pass through the guidance structure and out the opening upon application of motive force to the analyte sensor thereby placing the analyte sensor into the inserted position; and
a coupling device positioned on or in the sensor insertion guidance structure and adapted to facilitate a communicative coupling of the analyte sensor to the microcontroller while the analyte sensor is in the inserted position;
wherein the analyte sensor is in contact with the sensor insertion guidance structure prior to insertion of the analyte sensor into skin; and
wherein the RSA is removably secured to the DSA housing prior to and during the passing of the analyte sensor out the opening in the DSA housing.

31. The resposable sensor assembly of claim 30 wherein the coupling device is positioned and adapted to facilitate the communicative coupling of the analyte sensor to the microcontroller while the RSA housing is removably secured to the DSA housing.

32. The resposable sensor assembly of claim 30 wherein the analyte sensor is disposed entirely within the DSA housing prior to being placed in the inserted position.

33. The resposable sensor assembly of claim 30 wherein the analyte sensor is at least partially extended from the DSA housing prior to being placed in the inserted position.

34. The resposable sensor assembly of claim 30 wherein the RSA and DSA are configured to be coupled with one another prior to the analyte sensor being placed in the inserted position and to remain coupled with one another while the analyte sensor is being placed in the inserted position.

* * * * *